United States Patent
Lin et al.

(10) Patent No.: US 10,857,267 B2
(45) Date of Patent: *Dec. 8, 2020

(54) ABSORBABLE IRON-BASED ALLOY IMPLANTABLE MEDICAL DEVICE

(71) Applicant: LIFETECH SCIENTIFIC (SHENZHEN) CO., LTD, Shenzhen (CN)

(72) Inventors: Wenjiao Lin, Shenzhen (CN); Li Qin, Shenzhen (CN); Deyuan Zhang, Shenzhen (CN); Hongtao Sun, Shenzhen (CN); Gui Zhang, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 18 days.

This patent is subject to a terminal disclaimer.

(21) Appl. No.: 15/763,329

(22) PCT Filed: Jun. 8, 2016

(86) PCT No.: PCT/CN2016/085188
§ 371 (c)(1),
(2) Date: Mar. 26, 2018

(87) PCT Pub. No.: WO2017/067181
PCT Pub. Date: Apr. 27, 2017

(65) Prior Publication Data
US 2018/0264178 A1    Sep. 20, 2018

(30) Foreign Application Priority Data
Oct. 19, 2015   (CN) .......................... 2015 1 0680062

(51) Int. Cl.
*A61L 31/02*   (2006.01)
*A61L 31/10*   (2006.01)
(Continued)

(52) U.S. Cl.
CPC .......... *A61L 31/022* (2013.01); *A61L 27/042* (2013.01); *A61L 27/34* (2013.01); *A61L 27/50* (2013.01);
(Continued)

(58) Field of Classification Search
None
See application file for complete search history.

(56) References Cited

U.S. PATENT DOCUMENTS

2006/0173528 A1* 8/2006 Feld ..................... A61F 2/91
623/1.15
2007/0224244 A1   9/2007 Weber et al.
(Continued)

FOREIGN PATENT DOCUMENTS

CN    101721266 A      6/2010
CN    102228721 A  * 11/2011
(Continued)

OTHER PUBLICATIONS

Machine translation for CN 102228721 A, Nov. 2, 2011. (Year: 2011).*
(Continued)

*Primary Examiner* — Carlos A Azpuru
*Assistant Examiner* — Casey S Hagopian
(74) *Attorney, Agent, or Firm* — Maier & Maier, PLLC

(57) ABSTRACT

An absorbable iron-based alloy implantable medical device includes an iron-based alloy matrix, a degradable polymer coating disposed on the surface of the iron-based alloy matrix, and a corrosion inhibition layer disposed on the surface of the iron-based alloy matrix. The corrosion inhi-
(Continued)

bition layer can delay early-stage corrosion of the iron-based alloy matrix, ensure mechanical performance of a medical device in the early stage of the implantation, prevent degradation of a polymer in the early stage of the implantation of the medical device, and reduce the usage of the degradable polymer, thereby reducing risks of inflammatory reactions.

9 Claims, 1 Drawing Sheet

(51) Int. Cl.
- *A61L 31/16* (2006.01)
- *A61L 31/14* (2006.01)
- *A61L 27/58* (2006.01)
- *A61L 27/04* (2006.01)
- *A61L 27/50* (2006.01)
- *A61L 27/54* (2006.01)
- *A61L 27/34* (2006.01)
- *A61L 31/08* (2006.01)

(52) U.S. Cl.
CPC ............... *A61L 27/54* (2013.01); *A61L 27/58* (2013.01); *A61L 31/10* (2013.01); *A61L 31/14* (2013.01); *A61L 31/148* (2013.01); *A61L 31/16* (2013.01); *A61L 31/082* (2013.01); *A61L 2400/18* (2013.01); *A61L 2420/08* (2013.01)

(56) References Cited

U.S. PATENT DOCUMENTS

| | | | |
|---|---|---|---|
| 2009/0192594 A1* | 7/2009 | Borck | A61L 31/10 623/1.46 |
| 2010/0087916 A1* | 4/2010 | Bayer | A61L 31/022 623/1.46 |
| 2010/0256747 A1* | 10/2010 | Hausbeck | A61L 31/022 623/1.46 |
| 2011/0282437 A1 | 11/2011 | Warner et al. | |
| 2014/0277396 A1 | 9/2014 | Mendelson et al. | |

FOREIGN PATENT DOCUMENTS

| | | |
|---|---|---|
| CN | 102228721 A | 11/2011 |
| CN | 104587534 A | 5/2015 |
| CN | 104758087 A | 7/2015 |

OTHER PUBLICATIONS

Burg, K. Natural and Synthetic Biomedical Polymers, Chapter 6 Poly(alpha-ester)s, 2014, pp. 115-121. (Year: 2014).*
International Search Report dated Sep. 14, 2016 of corresponding International application No. PCT/CN2016/085188; 8 pgs.
Xu, Binshi et al., "Grease-Like Rust-Resisting Material", China Materials Engineering Canon: Materials Surface Engineering II, vol. 17, Dec. 31, 2006 (Dec. 31, 2006), pp. 446-451.
Chinese Office Action dated Jan. 3, 2019, in connection with corresponding CN Application No. 201510680062.6 (26 pgs., including machine-generated English translation).
Office Action dated Jul. 2, 2020 in corresponding European Application No. 16 856 622.2; 6 pages.

* cited by examiner

ABSORBABLE IRON-BASED ALLOY IMPLANTABLE MEDICAL DEVICE

FIELD

The present application belongs to the field of absorbable implanted medical devices, and more particularly relates to an absorbable iron-based alloy implanted medical device.

BACKGROUND

At present, materials for a biological absorbable implanted medical device mainly include polymers, a magnesium-based alloy and an iron-based alloy. The most frequently applied polymer is polylactic acid, which can be completely degraded and absorbed, with degradation products of carbon dioxide and water, but its mechanical property is poor. The size of the polymer-based device should be larger than that of the metal-based device so that the polymer-based device have the same mechanical property as a metal-based device, which limits application of the polymer-based device. The magnesium-based alloy and the iron-based alloy have advantages of easiness in processing and molding and high mechanical strength. However, as the magnesium-based alloy is corroded too fast in a human body, it needs to enlarge the size of a magnesium-based alloy device to obtain the mechanical property in the early stage of implantation, and in this way, the application of the magnesium-based alloy is limited as well.

In terms of clinical application, when the absorbable implanted medical device fulfills its expected use, after a diseased portion is cured and is recovered to its normal shape and function (cured), on the premise of not causing a new biological compatibility problem, the shorter the time that the device is completely degraded and absorbed by an organ the better. According to different portions to which the device is clinically applied, the recovery period is generally considered as 1 to 6 months, and within this period of time, the device is required to keep a structural integrity and have a sufficient mechanical property. The iron-based alloy has a good biological compatibility, and iron ions contribute to inhibiting smooth muscles and promoting growth of endothelial cells, but due to the slow corrosion of the iron-based alloy in the body, an iron-based alloy device would be completely corroded for a long time after the diseased portion is cured; and therefore, it is necessary to accelerate corrosion to shorten the corrosion cycle of the iron-based alloy.

The degradation products of some degradable polymers are acidic. If the surface of the iron-based alloy is coated with a degradable polymer of this type, its corrosion speed would be increased. Degradation of the degradable polymer in the body would lower the pH value of a local microenvironment near a device implantation position, thereby forming a local micro acidic environment where the iron-based alloy is corroded faster to generate iron salt and/or iron oxides and/or iron hydroxides serving as corrosion products.

For the iron-based alloy device of a predetermined specification, the corrosion speed and the corrosion cycle of an iron-based alloy substrate are determined according to the amount, the type and the nature of the degradable polyester. In order to ensure that the iron-based alloy substrate would be completely corroded within predetermined time, more degradable polymers would be used, but as their degradation products are acidic, an inflammatory reaction risk would be increased. In addition, under conditions that the type and the nature of the degradable polymer have been selected and the amount of the degradable polymer is sufficent to completely corrode the iron-based alloy substrate, extremely high corrosion speed or local severe corrosion of the iron-based alloy would affect the structural integrality and the mechanical property of the iron-based alloy device in the early stage of implantation (1 to 6 months, namely the above-mentioned recovery period), thereby it is hard for the device to meet a requirement for clinical application. These defects are specifically as follows: (1) the degradation products of the degradable polymer are acidic, and there are small molecular residues with a higher degradation speed in the degradable polymer(for example, the standard monomer residue amount of the polylactic acid is less than 2%), that will result in faster corrosion of the iron-based substrate in the early stage of implantation, for example, after the device is implanted into a coronary artery for about 1 to 7 days, excessively fast corrosion and accumulation of the corrosion products cause incomplete endothelialization of the inner surface of the device, which increases a risk of acute thrombosis and subacute thrombosis; and (2) the heterogeneity of degradable polymer degradation easily leads to non-uniform corrosion of the iron-based alloy substrate, and local fast corrosion possibly results in breakage, which leads to a fact that it is hard for the iron-based alloy substrate to meet requirements on a structural integrality and a mechanical property in the early stage. Although the excessively fast corrosion of the iron-based alloy device in the early stage of implantation can be prevented by reducing the amount of the degradable polymer, the corrosion cycle of the iron-based alloy device would be prolonged. Therefore, for the iron-based alloy device including the degradable polymer, under the conditions that the type and the nature of the degradable polymer and a amount ratio of the degradable polymer to the iron-based alloy are determined, it is necessary to seek a way to reduce the early corrosion speed of the iron-based substrate in the acidic environment formed by the degradable polyester to guarantee the mechanical property of the device in the early stage of implantation and a way to reduce the amount of the degradable polymer by effective use of the degradable polymer.

SUMMARY

In view of this, the present application provides an absorbable iron-based implanted medical device. After being implanted into a body, the absorbable iron-based implanted medical device is corroded slowly or is even totally not corroded within 1 to 6 months, and can meet a clinical requirement on a mechanical property of the device in the early stage of implantation. In addition, under a condition of maintaining its preset corrosion cycle, the amount of a degradable polymer can be reduced.

An absorbable iron-based alloy implanted medical device is provided, including: an iron-based alloy substrate, a degradable polymer disposed on the surface of the iron-based alloy substrate, and a corrosion inhibition layer disposed on the surfaces of the iron-based alloy substrate and the degradable polymer.

The degradable polymer may cover all surface of the iron-based alloy substrate and may also cover part of the surface of the iron-based alloy substrate. When the degradable polymer covers all the surface of the iron-based alloy substrate, the corrosion inhibition layer covers at least part of surface of the degradable polymer. When the degradable polymer does not cover all the surface of the iron-based alloy substrate, the corrosion inhibition layer may only cover at least part of the surface of the degradable polymer, or the corrosion inhibition layer and the degradable polymer may cover different surface of the iron-based alloy substrate in a staggering manner, or the corrosion inhibition layer covers at least part of the surface of the degradable polymer and cover at least part of non-covered region.

A material of the iron-based alloy substrate may be an iron-based alloy with a carbon content less than or equal to 2.11 wt. % or pure iron.

The degradable polymer is selected from degradable polyester and/or degradable polyanhydride. The degradable polyester is selected from the group consisting of polylactic acid, polyglycolic acid, poly(lactic acid-glycolic acid), polycaprolactone, polyhydroxyalkanoate, polyacrylate, poly(ethylene succinate), poly(β-hydroxybutyrate) and polyethylene glycol adipate, or is a physical blend of at least two of the polylactic acid, the polyglycolic acid, the poly(ethylene succinate), the poly (β-hydroxybutyrate), the polycaprolactone, the polyethylene glycol adipate, a polylactic acid-glycollic acid copolymer and a polyhydroxybutyrate-pentanoate copolymer, or is selected from the group consisting of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycollic acid copolymer and the polyhydroxybutyrate-pentanoate copolymer. The degradable polyanhydride is selected from the group consisting of poly1,3-bis(p-carboxyphenoxy) propane-sebacic acid, poly(erucic acid dimer-sebacic acid) or poly(fumaric acid-sebacic acid), or the degradable polymer is a copolymer formed by copolymerizing at least two of monomers forming the above degradable polyester and the above degradable polyanhydride.

An active drug is mixed into the degradable polymer, or no active drug is mixed. The active drug may be a drug for inhibiting vascular proliferation, such as taxol, sirolimus and its derivative, or an antiplatelet drug such as cilostazol, or an antithrombotic drug such as heparin, or an anti-inflammatory reaction drug such as dexamethasone, or a mixture of the above several drugs.

A material of the corrosion inhibition layer is an organic matter including at least one hydrophobic group.

The organic matter is selected from the group consisting of a mixture of solid alkane and semisolid alkane, the solid alkane, the semisolid alkane, higher fatty glyceride, lipoid, higher alkanol, higher fatty acid and its salt, an organic acid esterified compound, polysiloxane, fat-soluble vitamin, a silane coupling agent, a linear alkyl compound or an amino acid.

The higher fatty glyceride is selected from the group consisting of monoglyceride, diglyceride or triglyceride; the lipoid is lecithin; the higher alkanol is selected from the group consisting of octacosanol and triacontanol; the higher fatty acid and its salt are selected from the group consisting of lauric acid, palmitic acid, stearic acid, magnesium stearate and octadecylamine; the organic acid esterified compound is selected from the group consisting of citrate, laurate and sucrose laurate; the polysiloxane is silicone oil; the fat-soluble vitamin is selected from the group consisting of β-carotenoid, vitamin E and vitamin A; the solid or semi-solid alkane is selected from the group consisting of paraffin, microcrystalline wax and VASELINE® (petroleum jelly); the linear alkyl compound is selected from the group consisting of sodium dodecyl sulfonate, sodium dodecyl sulfate, dodecyl dimethyl benzyl ammonium chloride and hexadecyl trimethyl ammonium chloride; and the amino acid is selected from the group consisting of leucine and alanine.

The absorbable iron-based alloy implanted medical device further includes a drug-loading layer which is disposed on the outermost layer of the medical device and includes a degradable polymer and an active drug.

Compared with the prior art, the absorbable iron-based alloy implanted medical device provided by the present application includes a corrosion inhibition layer. After the device is implanted into a body for a period of time, the corrosion inhibition layer may effectively prevent seepage of water molecules and inhibit formation of a micro acidic environment on the surface of the iron-based alloy substrate, thus avoiding occurrence of problems of too fast corrosion, local severe corrosion and the like of the iron alloy substrate in the early stage of implantation and ensuring that the iron-based alloy medical device meets a clinical mechanical property requirement in the initial stage of implantation. As the corrosion inhibition layer covers the degradable polymer, degradation consumption of the degradable polymer in a body fluid environment in the initial stage of implantation may be greatly reduced, and the utilization rate of the degradable polymer is increased. On the premise of guaranteeing the same corrosion cycle, the amount of the degradable polymer may be reduced, which lowers an inflammation risk. With the gradual degradation consumption or metabolic transferring of the material of the corrosion inhibition layer, the degradable polymer on the surface of the iron-based alloy substrate is gradually hydrolyzed to form the micro acidic environment, thereby accelerating the corrosion of the iron-based alloy substrate. The absorbable iron-based alloy implanted medical device has a decreased design size, and produces a decreased amount of corrosion products after being implanted, facilitating faster absorption or elimination of the corrosion products of the iron-based alloy substrate.

DETAILED DESCRIPTION

In order to facilitate understanding of the present application, a more comprehensive description is made to the present application in connection with accompanying drawing as follows. A preferred embodiment of the present application is as shown in the figures. However, the present application may be implemented in many different forms, not limited to the embodiments described herein. On the contrary, these embodiments provided are intended to make disclosed contents of the present application more thorough and comprehensive.

Unless otherwise defined, all technical and scientific terms used in the text have the same meanings of general understandings of persons skilled in the art of the present application. Terms used in the description of the present application in the text are only intended to describe the specific embodiments, but not to limit the present application.

Figure 1:
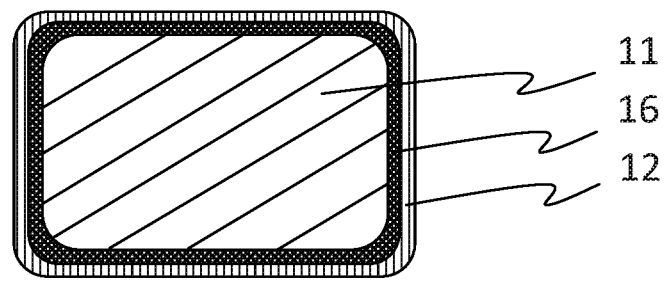
FIG. 1 is a section schematic diagram of an absorbable implanted medical device provided by an implementation mode of the present application along its lengthwise direction.

There are various position relations between a degradable polymer and an iron-based alloy substrate as well as between a corrosion inhibition layer and the degradable polymer and between the corrosion inhibition layer and the iron-based alloy substrate. As an implementation mode, as shown in FIG. 1, a degradable polymer coating 16 completely covers the surface of the iron-based alloy substrate 11; an active drug may be mixed into the degradable polymer coating 16; and the corrosion inhibition layer 12 also completely covers the degradable polymer coating 16.

Figure 2:
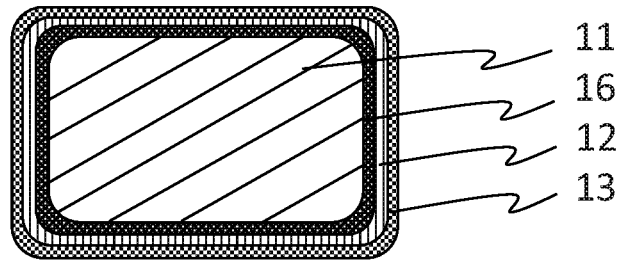
FIG. 2 is a section schematic diagram of an absorbable implanted medical device provided by another implementation mode of the present application along its lengthwise direction.

A drug-loading layer is further disposed on the outermost layer of the surface of the absorbable iron-based alloy implanted medical device. As shown in FIG. 2, the drug-loading layer 13 completely covers the surface of the corrosion inhibition layer 12.

A material of the iron-based alloy substrate 11 may be pure iron or an iron-based alloy with a carbon content less than or equal to 2.11 wt. %, such as a product obtained by carburizing and/or nitriding the pure iron.

Degradation of a degradable polymer in a body fluid environment would produce an acidic carboxy group which forms a local micro acidic environment, thereby accelerating corrosion of the iron-based alloy substrate 11. The larger the amount of the degradable polymer coating 16 the faster the corrosion of the iron-based alloy substrate 11. The corrosion cycle of the iron-based alloy implanted medical device may be adjusted by adjusting parameters, such as the material, the thickness, the molecular weight and the crystallinity of the degradable polymer coating 16.

In the early stage of implantation of the medical device, the corrosion inhibition layer 12 may effectively prevent seepage of water molecules and inhibit formation of the micro acidic environment on the surface of the iron-based alloy substrate, thus avoiding occurrence of problems of too fast early corrosion, local severe corrosion and the like of the iron alloy substrate 11 and guaranteeing a mechanical property of the medical device in the early stage of implantation. The corrosion inhibition layer 12 is disposed on the outer layer of the degradable polymer and is configured to isolate the degradable polymer from water to effectively delay its degradation and increase its utilization rate, thereby reducing the amount of the degradable polymer. As the implantation time goes by, the corrosion inhibition layer 12 is gradually consumed, and the degradable polymer is gradually degraded, leading to the formation of the micro acidic environment which may accelerate the corrosion of the medical device in the later stage of implantation. The effective supporting time of the medical device may be adjusted by adjusting the thickness of the corrosion inhibition layer 12.

The drug-loading layer 13 is configured to load a drug to further treat a portion where the device is implanted, and it includes a degradable polymer and an active drug.

Degradable polymer materials in the degradable polymer coating 16 and the drug-loading layer 13 at least include one degradable polymer which produces acidic degradation products, such as carboxylic acid, after being degraded. The degradable polymer is selected from degradable polyester and/or degradable polyanhydride. The degradable polyester is selected from the group consisting of polylactic acid, polyglycolic acid, poly(lactic acid-glycolic acid), polycaprolactone, polyhydroxyalkanoate, polyacrylate, poly(ethylene succinate), poly (β-hydroxybutyrate) and polyethylene glycol adipate, or is a physical blend of at least two of the polylactic acid, the polyglycolic acid, the poly(ethylene succinate), the poly(β-hydroxybutyrate), the polycaprolactone, the polyethylene glycol adipate, a polylactic acid-glycolic acid copolymer and a polyhydroxybutyrate-pentanoate copolymer, or is selected from the group consisting of copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycolic acid copolymer and the polyhydroxybutyrate-pentanoate copolymer. The degradable polyanhydride is selected from the group consisting of poly1,3-bis(p-carboxyphenoxy)propane-sebacic acid, poly (erucic acid dimer-sebacic acid) or poly(fumaric acid-sebacic acid), or the degradable polymer is a copolymer formed by copolymerizing at least two of monomers forming the above degradable polyester and the above degradable polyanhydride.

The active drug may be a drug for inhibiting vascular proliferation, such as taxol, sirolimus and its derivative, or an antiplatelet drug such as cilostazol, or an antithrombotic drug such as heparin, or an anti-inflammatory reaction drug such as dexamethasone, or a mixture of the above several drugs.

The degradable polymer coating, the corrosion inhibition layer and the drug-loading layer are coated in a way of spray coating, dip coating, brush coating and electrostatic spinning The absorbable iron-based alloy implanted medical device of the present application may be a blood vessel stent, an orthopedic implant, a gynecological implant, an andrological implant, a respiratory implant and an orthopedic implant.

By taking an iron-based alloy coronary artery stent as an example, a further detailed description is made to the present application in combination with specific embodiments as follows, but not intended to limit the scope of protection of the present application.

It should be noted that animal experiments in all the embodiments as follows show that under the action of the corrosion inhibition layer, the iron-based alloy stent is slowly corroded within 1 to 6 months of the early stage of implantation. The internal corrosion state of the iron-based alloy stent and whether a mechanical property requirement in the early stage is met or not are expressed by main measures of executing euthanasia to animals in which the stents are placed at different observation time points, such as 3 months, 6 months, 12 months, 2 years and 3 years, and then each stent and a tissue of a portion where the stent is placed are taken out and a radial supporting strength and mass loss test are conducted on the stent and a blood vessel segment where the stent is placed.

Clinically, the diastolic pressure (low pressure) and the systolic pressure (high pressure) of a coronary vessel of a normal person are 60 to 120 mmHg, but the systolic pressure of a hypertension patient is up to 175 mmHg, namely 23.3 kPa. In case of coronary artery spasm, the systolic pressure of the vessel is 400 mmHg, namely 55 kPa. A psychological stress state, a cold stimulation, a strenuous exercise, coronary atherosclerosis and a local stimulation to the coronary artery due to coronary angiogram as well as one-time heavy smoking or drinking may all induce the coronary artery spasm. Thus, in order to realize an effective support for the coronary vessel, the stent may at least bear the systolic pressure of 23.3 kPa in case of pulsation of the coronary vessel, and had better bear the systolic pressure of 55 kPa in case of vasospasm. A way of testing the radial strength of the stent is as follows: uniformly applying a radial pressure to the stent through a compression module to compress the stent to generate a uniform deformation. It is defined that the radial pressure intensity applied when the stent deforms by 10 percent in a radial direction (the outer diameter) is the radial strength of the stent. The radial supporting strength test is carried out with a radial supporting strength tester (RX550-100) produced by the MSI company: the stent implanted into the body of the animal and the blood vessel are taken out, the surface is dried, and then the test is directly carried out, thus the radial supporting strengths of the stent at different time points after the stent is implanted is obtained.

A way of testing the weight loss is as follows: an iron-based alloy stent (with a degradable polymer) including an iron-based alloy substrate (which is a bare stent without the degradable polymer) with the mass of $M_0$ is implanted into an abdominal aorta of a rabbit, the iron-based alloy stent implanted into the body of the animal and a tissue where the stent is placed are taken out at a preset observation time point, then the tissue and the stent are soaked in 1 mol/L sodium hydroxide solution to digest the tissue, if there is a tannic acid chemical conversion film remained on the surface of the iron-based substrate, it is removed, then the iron-based alloy stent or a fragment thereof is taken out of the solution, and it is put into a solution at a certain concentration (such as a tartaric acid solution at the concentration of 3 percent, and/or an organic solution) for ultrasonic treatment to enable a corrosion product on its surface and the polymer layer to completely fall into or be dissolved in the solution, the residual non-corroded iron-based alloy stent or fragment thereof was taken out of the solution, and it is dried and weighted, and the mass is recorded as $M_t$. A mass loss rate W is represented by a percentage of a difference value of the weight loss of a corroded and cleaned stent lever to the weight of the iron-based substrate, as shown in Formula 1:

$$W=(M_t-M_0)/M_0\times100\% \quad (1)$$

W represents the mass loss rate $M_t$ represents the mass of the residual iron-based alloy stent substrate after corrosion $M_0$ represents the initial mass of the iron-based alloy stent substrate wherein when the mass loss rate W of the iron-based alloy substrate is less than 5 percent, it is defined that no corrosion occurs; and when the mass loss rate W of the iron-based alloy substrate is greater than or equal to 90 percent, it is defined that complete corrosion occurs.

The design target of the iron-based alloy stent provided by each embodiment as follows is to meet the following clinical requirements: after being implanted, the iron-based alloy stent may provide effective supporting for 3 months; after 3 months of implantation, the radial supporting strength is higher than or equal to 55 kPa; and the corrosion cycle is longer than 6 months but shorter than or equal to 24 months.

The definition of the stent of the specification 30008 in each embodiment is as follows: after the stent is expanded under the action of a nominal expansion pressure of 8 atm, the nominal diameter is 3 mm, and the nominal length is 8 mm.

It should be noted that in each embodiment as follows, a normal fluctuation of the own performance of a stent product within a designed allowable range, an individual difference of the animal, an insufficient density of designed sampling points and a system error unavoidably introduced by the test ways may lead to fluctuations of monitored stent radial strength data and complete corrosion time points within a certain range in an actual test.

Embodiment 1

A polished iron-based alloy coronary artery stent of the specification 30008, which is subjected to nitriding, is selected, with its original radial strength of 145 kPa and mass of 4.5 mg; the surface of a stent matrix is coated with a poly-dl-lactic acid-ethyl acetate solution in a way of spray coating; after the surface is dried, a degradable poly-dl-lactic acid coating which completely covers the surface of the stent and has a thickness of 6 μm is manufactured; and the surface of the stent manufactured in the above steps is coated with an octacosanol-trichloromethane solution in the way of spray coating, thereby an octacosanol corrosion inhibition layer which completely covers the degradable poly-dl-lactic acid coating and has a thickness of 2 μm is formed. The iron-based absorbable stent manufactured by the above steps is implanted into an abdominal aorta of a rabbet; after 3 months, it is taken out, and it is found that endothelialization of the stent is complete, no early thrombus and inflammation phenomena are caused, and its radial supporting strength is 80 kPa; and the complete corrosion cycle monitored in the experiments of the same group of animals is 12 months.

Embodiment 2

A polished iron-based alloy coronary artery stent substrate of the specification 30008, which is subjected to nitriding, is selected, with its original radial strength of 145 kPa and mass of 4.5 mg; the surface of the stent substrate is coated with a poly-dl-lactic acid-ethyl acetate solution in a way of spray coating; after the surface is dried, a degradable poly-dl-lactic acid coating which completely covers the surface of the stent and has a thickness of 10 μm is manufactured; and the surface of the stent manufactured in the above steps is coated with a tristearin-trichloromethane solution in the way of spray coating, thereby a tristearin corrosion inhibition layer which completely covers the degradable poly-dl-lactic acid coating and has a thickness of 2 μm is formed. The iron-based absorbable stent manufactured by the above steps is implanted into an abdominal aorta of a rabbet; after 3 months, it is taken out, and it is found that endothelialization of the stent is complete, no early thrombus and inflammation phenomena are caused, and its radial supporting strength is 80 kPa; and the complete corrosion cycle monitored in the experiments of the same group of animals is 6 months.

Embodiment 3

A polished iron-based alloy coronary artery stent substrate of the specification 30008, which is subjected to nitriding, is selected, with its original radial strength of 145 kPa and mass of 4.5 mg; the surface of the stent substrate is coated with a poly-dl-lactic acid-ethyl acetate solution in a way of spray coating; after the surface is dried, a degradable poly-dl-lactic acid coating which completely covers the surface of the stent and has a thickness of 6 μm is manufactured; and the surface of the stent manufactured by the above steps is coated with an octacosanol-trichloromethane solution in the way of spray coating, thereby an octacosanol corrosion inhibition layer which completely covers the degradable poly-dl-lactic acid coating and has a thickness of 5 μm is formed. The absorbable iron-based stent manufactured by the above steps is implanted into an abdominal aorta of a rabbet; after 3 months, it is taken out, and it is found that endothelialization of the stent is complete, no early thrombus and inflammation phenomena are caused, and its radial supporting strength is 110 kPa; and the complete corrosion cycle monitored in the experiments of the same group of animals is 18 months.

Embodiment 4

A polished iron-based alloy coronary artery stent substrate of the specification 30008, which is subjected to nitriding, is selected, with its original radial strength of 145 kPa and mass of 4.5 mg; the surface of the stent substrate is coated with a poly-dl-lactic acid-ethyl acetate solution in a way of spray coating; after the surface is dried, a degradable poly-dl-lactic acid coating which completely covers the surface of the stent and has a thickness of 6 μm is manufactured; the surface of the stent manufactured through the above steps is coated with vitamin E oil in a way of brush coating, thereby a vitamin E oil corrosion inhibition layer which completely covers the degradable poly-dl-lactic acid coating and has a thickness of 2 μm is formed; the surface of the vitamin E oil corrosion inhibition layer is coated with a poly-dl-lactic acid-sirolimus-ethyl acetate solution in the way of spray coating, and the mass ratio of poly-dl-lactic acid to sirolimus is 2 to 1; after the surface is dried, a poly-dl-lactic acid-sirolimus drug-loading layer which has a thickness of 3 μm is manufactured. The absorbable iron-based stent manufactured by the above steps is implanted into an abdominal aorta of a rabbet; after 3 months, it is taken out, and it is found that endothelialization of the stent is complete, no early thrombus and inflammation phenomena are caused, and its radial supporting strength is 80 kPa; and the complete corrosion cycle monitored in the experiments of the same group of animals is 12 months.

Embodiment 5

A polished iron-based alloy coronary artery stent substrate of the specification 30008, which is subjected to nitriding, is selected, with its original radial strength of 145 kPa and mass of 4.5 mg; the surface of the stent substrate is coated with a poly-dl-lactic acid-ethyl acetate solution in a way of spray coating; after the surface is dried, a degradable poly-dl-lactic acid coating which completely covers the surface of the stent and has a thickness of 6 μm is manufactured; and the surface of the stent manufactured by the above steps is coated with lecithin-ethanol solution, thereby a lecithin corrosion inhibition layer which covers 90 percent of the surface of the degradable poly-dl-lactic acid coating and has a thickness of 2 μm is formed. The absorbable iron-based stent manufactured by the above steps is implanted into an abdominal aorta of a rabbet; after 3 months, it is taken out, and it is found that endothelialization of the stent is complete, no early thrombus and inflammation phenomena are caused, and its radial supporting strength is 80 kPa; and the complete corrosion cycle monitored in the experiments of the same group of animals is 12 months.

Embodiment 6

A polished iron-based alloy coronary artery stent substrate of the specification 30008, which is subjected to nitriding, is selected, with its original radial strength of 145 kPa and mass of 4.5 mg; the surface of the stent substrate is coated with a poly-dl-lactic acid-ethyl acetate solution in a way of spray coating; after the surface is dried, a degradable poly-dl-lactic acid coating which covers 90 percent of the surface of the stent and has a thickness of 6 μm is manufactured; the surface of the stent manufactured by the above steps was coated with a sodium stearate-trichloromethane solution in the way of spray coating, thereby forming a sodium stearate corrosion inhibition layer which covers 90 percent of the surface of the degradable poly-dl-lactic acid coating and has a thickness of 2 μm is formed, wherein 80 percent of the sodium stearate corrosion inhibition layer covers the surface of the degradable poly-dl-lactic acid coating, and 10 percent of the sodium stearate corrosion inhibition layer directly covers the surface of the iron stent. The absorbable iron-based stent manufactured by the above steps is implanted into an abdominal aorta of a rabbet; after 3 months, it is taken out, and it is found that endothelialization of the stent is complete, no early thrombus and inflammation phenomena are caused, and its radial supporting strength is 80 kPa; and the complete corrosion cycle monitored in the experiments of the same group of animals is 18 months.

Contrast 1

A polished iron-based alloy coronary artery stent substrate of the specification 30008, which is subjected to nitriding, is selected, with its original radial strength of 145 kPa and mass of 4.5 mg; the surface of the stent is coated with a poly-dl-lactic acid-ethyl acetate solution in a way of spray coating; and after the surface is dried, a degradable poly-dl-lactic acid coating which completely covers the surface of the stent and has a thickness of 6 μm is manufactured. The stent is implanted into an abdominal aorta of a rabbet; after 3 months, it is taken out, and it is found that the stent is locally severely corroded, and its radial supporting force is lower than 55 kPa; and the complete corrosion cycle monitored in the experiments of the same group of animals is 11 months.

Contrast 2

A polished iron-based alloy coronary artery stent substrate of the specification 30008, which is subjected to nitriding, is selected, with its original radial strength of 145 kPa and mass of 4.5 mg; the surface of the stent is coated with a tristearin-trichloromethane solution in a way of spray coating, thereby a tristearin corrosion inhibition layer which completely covers the surface of the stent and has a thickness of 2 μm is formed; the surface of the tristearin corrosion inhibition layer manufactured by the above step is coated with a poly-dl-lactic acid-ethyl acetate solution; and after the surface is dried, a degradable poly-dl-lactic acid coating which has a thickness of 10 μm is manufactured and covers all surface of the tristearin corrosion inhibition layer. The stent is implanted into an abdominal aorta of a rabbet; after 3 months, it is taken out, and it is found that endothelialization of the stent is complete, no early thrombus and inflammation phenomena are caused, and its radial supporting force is 80 kPa; and the complete corrosion cycle monitored in the experiments of the same group of animals is 12 months.

Contrast 3

A polished iron-based alloy coronary artery stent substrate of the specification 30008, which is subjected to nitriding, is selected, with its original radial strength of 175 kPa and mass of 5.5 mg; the surface of the stent is coated with a poly-dl-lactic acid-ethyl acetate solution in a way of spray coating; and after the surface is dried, a degradable poly-dl-lactic acid coating which completely covers the surface of the stent and has a thickness of 10 μm is manufactured. The stent is implanted into an abdominal aorta of a rabbet; after 3 months, it is taken out, and it is found that the stent is locally severely corroded, and its radial supporting force is 80 kPa; and the complete corrosion cycle monitored in the experiments of the same group of animals is 12 months.

It can be seen from all the above embodiments that the absorbable iron-based alloy stents with the corrosion inhibition layers in the embodiments all realize delaying of the corrosion of the iron-based alloy substrate within a period that the corrosion inhibition layers play a protection role, and may all meet a 3-month mechanical property requirement in the early stage of implantation. By adjustment of the amounts of the corrosion inhibition layers in all the embodiments, comparison with Contrast 1 shows that the stents provided by Embodiments from 1 to 6 may guarantee the structural integralities and have sufficient mechanical supports after being implanted within 3 months. Comparison with Contrast 2 shows that on the premise that the stents provided by Embodiments of 1, 3, 4, 5 and 6 may guarantee the structural integralities and have sufficient mechanical supports after being implanted within 3 months, the amounts of the degradable polymers are smaller. Comparison with Contrast 3 shows that on the premise that the stents provided by Embodiments of 1, 2, 4 and 5 may guarantee the structural integralities and have sufficient mechanical supports after being implanted within 3 months, the masses of the iron-based alloy substrate are smaller, and it can be expected that fewer corrosion products are produced subsequently and the complete absorption cycle is shorter.

The above embodiments only express several implementation modes of the present application, and their descriptions are relatively specific and detailed, but not intended to limit the scope of the present application thereby. It should be noted that a person skilled in the art can make various deformations and improvements without departing from the concept of the present application, and these deformations and improvements shall all fall within the scope of protection of the present application. Thus, attached claims for the scope of protection of the present application shall prevail.

The invention claimed is:

1. An absorbable iron-based alloy implanted medical device, comprising:
    an iron-based alloy substrate;
    a degradable polymer covering all or part of the surface of the iron-based alloy substrate, the degradable polymer being hydrolysable to produce an acidic carboxy group to form a micro acid environment on said surface and being selected from group consisting of:
    a degradable polyester selected from the group consisting of polylactic acid; polyglycolic acid; poly(lactic acid-glycolic acid)("polylactic acid-glycolic acid copolymer"); polycaprolactone; polyhydroxyalkanoate; polyacrylate; poly(ethylene succinate); poly(β-hydroxybutyrate); polyethylene glycol adipate; a physical blend of at least two of: the polylactic acid, the polyglycolic acid, the poly(ethylene succinate), the poly(β-hydroxybutyrate), the polycaprolactone, the polyethylene glycol adipate, a polylactic acid-glycolic acid copolymer and a polyhydroxybutyrate-pentanoate copolymer; and copolymers formed by copolymerizing at least two of monomers forming the polylactic acid, the polyglycolic acid, the poly(ethylene succinate), the poly(β-hydroxybutyrate), the polycaprolactone, the polyethylene glycol adipate, the polylactic acid-glycolic acid copolymer and the polyhydroxybutyrate-pentanoate copolymer;
    a degradable polyanhydride being selected from the group consisting of poly1,3-bis(p-carboxyphenoxy)propane-sebacic acid; poly(erucic acid dimer-sebacic acid); and poly(fumaric acid-sebacic acid); and
    a copolymer formed by copolymerizing at least two monomers forming the degradable polyester and the degradable polyanhydride;
    an active drug mixed into the degradable polymer; and
    a corrosion inhibition layer disposed on the surface of the iron-based alloy substrate to prevent seepage of water molecules and inhibit formation of a micro acid environment on said surface,
    wherein the corrosion inhibition layer covers regions of the iron-based alloy substrate which are not covered by the degradable polymer and/or only part of the degradable polymer.

2. The absorbable iron-based alloy implanted medical device according to claim 1, wherein the iron-based alloy substrate comprises an iron-based alloy with a carbon content less than or equal to 2.11 wt. % of pure iron.

3. The absorbable iron-based alloy implanted medical device according to claim 1, wherein the corrosion inhibition layer comprises an organic matter including at least one hydrophobic group.

4. The absorbable iron-based alloy implanted medical device according to claim 3, wherein the organic matter is selected from the group consisting of a mixture of solid alkane and semisolid alkane, the solid alkane, the semisolid alkane, higher fatty glyceride, lipoid, higher alkanol, higher fatty acid and salt thereof, an organic acid esterified compound, polysiloxane, fat-soluble vitamin, a silane coupling agent, a linear alkyl and an amino acid.

5. The absorbable iron-based alloy implanted medical device according to claim 4, wherein the higher fatty glyceride is selected from the group consisting of monoglyceride, diglyceride or triglyceride; the lipoid is lecithin; the higher alkanol is selected from the group consisting of octacosanol and triacontanol; the higher fatty acid and salt thereof are selected from the group consisting of lauric acid, palmitic acid, stearic acid, magnesium stearate and octadecylamine; the organic acid esterified compound is selected from the group consisting of citrate, laurate and sucrose laurate; the polysiloxane is silicone oil; the fat-soluble vitamin is selected from the group consisting of β-carotenoid, vitamin E and vitamin A; the solid or semisolid alkane is selected from the group consisting of paraffin, microcrystalline wax and petroleum jelly; the linear alkyl compound is selected from the group consisting of sodium dodecyl sulfonate, sodium dodecyl sulfate, dodecyl dimethyl benzyl ammonium chloride and hexadecyl trimethyl ammonium chloride; and the amino acid is selected from the group consisting of leucine and alanine.

6. The absorbable iron-based alloy implanted medical device according to claim 1, wherein the degradable polymer into which the active drug is mixed into forms a drug-loading layer which is disposed on the outermost layer of the implanted medical device.

7. An absorbable iron-based alloy implanted medical device, comprising:
    an iron-based alloy substrate,
    a degradable polymer disposed on the surface of the iron-based alloy substrate, said degradable polymer being hydrolysable to produce an acid carboxy group to form a micro acid environment on said surface, and
    a corrosion inhibition layer disposed on the surface of the iron-based alloy substrate to prevent seepage of water molecules and inhibit formation of a micro acid environment on said surface, said corrosion inhibition layer comprising:
        a higher fatty glyceride selected from the group consisting of monoglyceride, diglyceride and triglyceride;
        lecithin;
        a higher alkanol selected from the group consisting of octacosanol and triacontanol;
        a higher fatty acid selected from the group consisting of lauric acid, palmitic acid, stearic acid, magnesium stearate and octadecylamine, and salts thereof;

an organic acid esterified compound selected from the group consisting of citrate, laurate and sucrose laurate;

silicone oil;

a fat-soluble vitamin is selected from the group consisting of β-carotenoid, vitamin E and vitamin A;

a solid or semisolid alkane is paraffin or microcrystalline wax and petroleum jelly;

a linear alkyl compound selected from the group consisting of sodium dodecyl sulfonate, sodium dodecyl sulfate, dodecyl dimethyl benzyl ammonium chloride and hexadecyl trimethyl ammonium chloride; or an amino acid selected from the group consisting of leucine and alanine.

8. The absorbable iron-based alloy implanted medical device according to claim 7, wherein the degradable polymer covers all surfaces of the iron-based alloy substrate, and the corrosion inhibition layer covers at least part of the surface of the degradable polymer.

9. The absorbable iron-based alloy implanted medical device according to claim 7, wherein the degradable polymer covers part of the surface of the iron-based alloy substrate, and the corrosion inhibition layer covers at least part of the surface of the degradable polymer; or the degradable polymer and the corrosion inhibition layer cover different surfaces of the iron-based alloy substrate in a staggered manner; or the corrosion inhibition layer covers at least part of the surface of the degradable polymer and covers at least part of regions which are not covered by the degradable polymer.

* * * * *